US009932280B2

(12) United States Patent
Bao et al.

(10) Patent No.: US 9,932,280 B2
(45) Date of Patent: Apr. 3, 2018

(54) SYNTHESIS OF OLEFINS FROM OXYGEN-FREE DIRECT CONVERSION OF METHANE AND CATALYSTS THEREOF

(71) Applicant: DALIAN INSTITUTE OF CHEMICAL PHYSICS, CHINESE ACADEMY OF SCIENCES, Dalian, Liaoning (CN)

(72) Inventors: Xinhe Bao, Liaoning (CN); Xiaoguang Guo, Liaoning (CN); Guangzong Fang, Liaoning (CN); Dehui Deng, Liaoning (CN); Hao Ma, Liaoning (CN); Dali Tan, Liaoning (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 200 days.

(21) Appl. No.: 14/003,551

(22) PCT Filed: Jul. 24, 2013

(86) PCT No.: PCT/CN2013/079977
§ 371 (c)(1),
(2) Date: Jan. 10, 2014

(87) PCT Pub. No.: WO2014/183337
PCT Pub. Date: Nov. 20, 2014

(65) Prior Publication Data
US 2014/0336432 A1    Nov. 13, 2014

(30) Foreign Application Priority Data
May 13, 2013    (CN) ............... 2013 1 0174960

(51) Int. Cl.
*B01J 23/75*    (2006.01)
*B01J 23/745*    (2006.01)
(Continued)

(52) U.S. Cl.
CPC ............... *C07C 2/84* (2013.01); *B01J 23/14* (2013.01); *B01J 23/34* (2013.01); *B01J 23/745* (2013.01);
(Continued)

(58) Field of Classification Search
CPC . B01J 21/08; B01J 23/745; B01J 23/75; B01J 23/755; B01J 27/20; B01J 27/22; B01J 27/224; B01J 27/24
See application file for complete search history.

(56) References Cited

U.S. PATENT DOCUMENTS 4,310,339 A * 1/1982 Blankenship ....... C03B 37/0142
118/729
4,579,750 A * 4/1986 Bowen ................... B01J 19/121
118/50.1
(Continued)

FOREIGN PATENT DOCUMENTS

CN    1167653 A    12/1997
CN    1491746 A    4/2004
(Continued)

OTHER PUBLICATIONS

Jen et al., "Acoustic Characterization of Silica Glasses," Journal of the American Ceramic Society 76(3), pp. 712-716, Mar. 1993.*
(Continued)

*Primary Examiner* — Jun Li
(74) *Attorney, Agent, or Firm* — Novick, Kim & Lee, PLLC; Allen Xue

(57) ABSTRACT

Provided is a method for the preparation of a metal lattice-doping catalyst in an amorphous molten state, and the
(Continued)

process of catalyzing methane to make olefins, aromatics, and hydrogen using the catalyst under oxygen-free, continuous flowing conditions. Such a process has little coke deposition and realizes atom-economic conversion. Under the conditions encountered in a fixed bed reactor (i.e. reaction temperature: 750~1200° C.; reaction pressure: atmospheric pressure; the weight hourly space velocity of feed gas: 1000~30000 ml/g/h; and fixed bed), conversion of methane is 8-50%. The selectivity of olefins is 30~90%. And selectivity of aromatics is 10~70%. There is no coking. The reaction process has many advantages, including a long catalyst life (>100 hrs), high stability of redox and hydrothermal properties under high temperature, high selectivity towards target products, zero coke deposition, easy separation of products, good reproducibility, safe and reliable operation, etc., all of which are very desirable for industrial application.

20 Claims, 2 Drawing Sheets

(51) Int. Cl.

| | | |
|---|---|---|
| *B01J 23/755* | (2006.01) | |
| *B01J 27/20* | (2006.01) | |
| *B01J 27/24* | (2006.01) | |
| *C07C 2/84* | (2006.01) | |
| *B01J 37/08* | (2006.01) | |
| *B01J 37/34* | (2006.01) | |
| *B01J 23/889* | (2006.01) | |
| *B01J 23/14* | (2006.01) | |
| *B01J 23/34* | (2006.01) | |
| *B01J 23/78* | (2006.01) | |
| *B01J 27/22* | (2006.01) | |
| *B01J 35/00* | (2006.01) | |
| *B01J 37/02* | (2006.01) | |
| *B01J 27/224* | (2006.01) | |

(52) U.S. Cl.
CPC ............ *B01J 23/75* (2013.01); *B01J 23/755* (2013.01); *B01J 23/78* (2013.01); *B01J 23/8892* (2013.01); *B01J 27/20* (2013.01); *B01J 27/22* (2013.01); *B01J 27/24* (2013.01); *B01J 35/002* (2013.01); *B01J 37/0201* (2013.01); *B01J 37/08* (2013.01); *B01J 37/348* (2013.01); *B01J 27/224* (2013.01); *C07C 2521/08* (2013.01); *C07C 2523/745* (2013.01); *C07C 2523/75* (2013.01); *C07C 2523/78* (2013.01)

(56) References Cited

U.S. PATENT DOCUMENTS

| | | | |
|---|---|---|---|
| 6,339,013 B1 | 1/2002 | Naseem et al. | |
| 7,559,494 B1* | 7/2009 | Yadav | A61L 27/06 241/22 |
| 2006/0210425 A1* | 9/2006 | Mirkarimi | C09D 4/00 422/400 |
| 2013/0180932 A1* | 7/2013 | Fukumura | B01J 27/24 210/749 |

FOREIGN PATENT DOCUMENTS

| | | |
|---|---|---|
| CN | 102020525 A | 4/2011 |
| CN | 102114421 A | 7/2011 |
| CN | 102614857 A | 8/2012 |

OTHER PUBLICATIONS

Rival et al., "Oxygen-Free Methane Aromatization in a Catalytic Membrane Reactor," Industrial & Engineering Chemistry Research 40(10), pp. 2212-2219, Apr. 2001.*
Auroux et al., "Acidic Character of Metal-Loaded Amorphous and Crystalline Silica-Aluminas Determined by XPS and Adsorption Calorimetry," The Journal of Physical Chemistry B 103(34), pp. 7195-7205, Aug. 1999.*
Mazdiyasni et al., "Synthesis, Characterization, and Consolidation of Si3N4 Obtained from Ammonolysis of SiCl4," Journal of the American Chemical Society 56(12), pp. 628-633, Dec. 1973.*
Yin et al., "Preparation and sintering of nano Fe coated Si3N4 composite powders," Journal of Central South University of Technology 16(2), pp. 184-189, Apr. 2009.*
Butov et al., "Refractive index dispersion of doped silica for fiber optics," Optics Communications 213(4-6), pp. 301-308, Dec. 2002.*
Zinfer R. Imsagilov et al., Direct conversion of methane on Mo/ZSM-5 catalysts to produce benzene and hydrogen: achievements and perspectives, Energy Environ. Sci., 2008, pp. 526-541.
Ulyana Zavyalova et al., Statistical Analysis of Past Catalytic Data on Oxidative Methane Coupling for New Insights into the Composition of High-Performance Catalysts, ChemCatChem, 2011, pp. 1-14.
Shuqi Ma et al., Recent progress in methane dehydroaromatization: From laboratory curiosities to promising technology, Journal of Energy Chemistry, 2013, 1-20.
C Méthivier et al., Pd/Si3N4 catalysis: preparation, characterization and catalytic activity for the methane oxidation, Applied Catalysis A:General, vol. 182, 2nd Issue, 1999, pp. 337-344.
L. O. O. Costa et al., Rh/CeO2—SiC catalyst for the partial oxidation of alcohol to hydrogen, Chinese Journal of Catalysis, 2013, pp. 257-262.

* cited by examiner

SYNTHESIS OF OLEFINS FROM OXYGEN-FREE DIRECT CONVERSION OF METHANE AND CATALYSTS THEREOF

FIELD OF THE INVENTION

The present invention is related to a method of olefins synthesis by oxygen-free direct conversion of methane under continuous flow conditions and the catalyst used, which presents no coke deposition and atom-economy conversion.

BACKGROUND OF THE INVENTION

Natural gas is an excellent clean energy resource, of which the primary component is methane ($CH_4$). The world appears to have abundant reserves of methane, especially with the recent discoveries of significant deposits of shale gas in continental North America and methane hydrate in the sediments of the ocean floors, which is estimated to be at least twice of the amount of carbon in all other known fossil fuel reserves.

Over the past few decades, both the production and the consumption of world natural gas have increased continuously. The proportion of natural gas in world primary energy production rose from 9.8% in 1950 to 24% at present, and was estimated to reach up to 29% in 2020. By that time, natural gas will become an important energy resource in the 21$^{st}$ century. However, the consumption of natural gas is still not mature, in the portion of natural gas used in chemical industry is low. Due to the difficulty of methane activation and the high cost of raw chemicals (olefin, aromatics etc.) caused by the fluctuating market of crude oil, the research of efficient methane conversion to valuable products is not only a scientific challenge but also an urgent need to alleviate the energy crisis and to ensure a sustainable development.

There are two basic routes to produce valuable chemicals from methane, indirect and direct conversion. Currently, the most widely used method is indirect conversion, i.e. methane is first converted to syngas with various C/H ratios by either reforming or partial oxidation, and then raw chemicals and refined oil products are converted from syngas through Fischer-Tropsch synthesis, syngas to olefin, syngas to gasoline, ammonia synthesis or many other processes. However, the indirect conversion of methane is always accompanied by complicated facilities, high production cost, and especially large $CO_2$ emission. Therefore, the study of direct methane conversion to valuable chemicals has received particular attention recently.

Direct conversion of methane can be classified into three routes currently: oxidative coupling of methane to ethylene (OCM), selective partial oxidation of methane to methanol and formaldehyde (SOM), and methane dehydroaromatization to aromatics (MDA). Keller and Bhasin from UCC reported the first case of the direct conversion of methane in 1982 that methane oxidative coupled to ethylene at 1023 K led to 14% of methane conversion and 5% of ethylene selectivity. Although this process has been optimized with methane conversion up to 20~40%, ethylene selectivity up to 50~80%, and ethylene yield of 14~25%, the scale-up application still suffer from many disadvantages such as high temperature oxidative condition, over oxidation of methane to $CO_2$, separation of products, etc. The SOM process encounters similar difficulties: methanol and formaldehyde tend to further oxidation and leads to low selectivity.

In 1993, researchers from Dalian Institute of Chemical Physics (DICP) reported methane dehydroaromatization (MDA) for the formation of aromatics (mainly $C_6H_6$) and $H_2$ at 973 K under non-oxidizing conditions in a flow reactor, using a zeolite catalyst (HZSM-5) modified with molybdenum, with the result of 6% of methane conversion and over 90% aromatics selectivity (exclusive of carbon deposit). Since this landmark discovery, many researchers have worked on this process, and a plentiful amount of encouraging progresses have been made in catalyst preparation, reaction mechanism, deactivation mechanism, and so on. Nevertheless, industrial applications are restricted by the rapid carbon deposition of the catalyst.

DETAILED DESCRIPTION OF THE INVENTION

The present invention is related to a method of olefins synthesis by oxygen-free direct conversion of methane under continuous flow conditions and its catalysts. The so-called oxygen-free conversion is that methane can be converted directly in absence of molecular oxygen ($O_2$), elemental sulfur (S), or sulfur oxide compounds (such as $SO_2$, etc.).

The said catalysts are that metal elements are doped in the lattice of amorphous-molten-state materials made from Si bonded with one or two of C, N and O element. The said doping is lattice doping. The so-called lattice doping is that the dopant metal elements exchange with the lattice elements in the doped materials, and the dopant metal elements may form or not form a specific chemical bonding (such as ionic bond, etc.) with other elements except the exchanged elements, which will lead to the metal dopant elements being confined in the lattice of the doped materials, resulting in a specific catalytic performance.

Taking the total weight of the catalyst as 100%, the amount of the dopant metal is more than 0.001 wt. % but less than 10 wt. %

The so-called amorphous-molten-state materials are that the metal and silicon-based materials are all in a molten state or surface in a molten state in the catalyst preparation, and then formed amorphous materials with long-range disorder and short-range order after being cooled.

Preferably, the dopant metal elements of the said catalysts are one or more of alkali metals, alkaline earth metals and transition metals.

Preferably, the said metal elements are one or more of Li, Na, K, Mg, Al, Ca, Sr, Ba, Y, La, Ti, Zr, Ce, Cr, Mo, W, Re, Fe, Co, Ni, Cu, Zn, Ge, In, Sn, Pb, Bi, Mn; and preferably one or more of Li, K, Mg, Al, Ca, Sr, Ba, Ti, Ce, Mn, Zn, Co, Ni, Fe.

Preferably, the types of the metal compounds are one or more of metal oxides, metal carbides, metal nitrides, metal silicides, and metal silicates.

The said catalysts are silicon-based materials that comprise one or more of O, C, and N, which is obtained by doping in its lattice metal dopants, forming a molten state, and solidifying the molten material.

Preferably, the precursors of dopant metal elements include one or more of elemental metals, nitrates, halides, sulfates, carbonates, hydroxides, metal carbonyls, organometallic alkoxide with 1 to 5 C atoms, and organic acid salts with 1 to 5 C atoms.

The silicon source for preparing silicon-based materials for doping includes liquid silicon source or solid silicon source.

The said liquid silicon source preferably include, but not limited to, one or more of tetraethyl silicates, silicon tetrachlorides and an organic silane compounds. The chemical formula of the organic silane compounds are as follows:

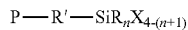 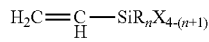

wherein
n=0, 1, 2;

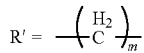

(m is 1 or ≥3),

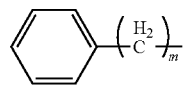

(m is 0, 1 or 2) or

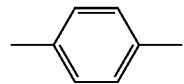

arylene, etc; R denotes one of hydroxyl group or methyl group; P=—Cl, —$NH_2$, —$HNCH_2CH_2NH_2$, —NHR (R denotes alkyl, alkenyl or aryl with 1 to 5 carbon atoms),

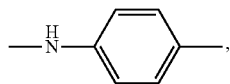

—$N_3$, —NCO, —SH, —CH=$CH_2$, —OCOCMe=$CH_2$,

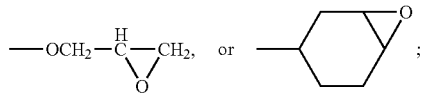

X denotes the carbon-containing functional groups which can be hydrolyzed or condensed, such as Cl, —OMe, —$OCH_2CH_3$, —$OCH_2CH_2OCH_3$, or —OAc.

The said solid silicon source preferably include, but not limited to, one or more of silica, silicon carbide, silicon nitride, elemental silicon, wherein, the particle size of the solid silicon source is preferably 10 nm-200 μm and the specific surface area is preferably 10-500 m²/g.

The preparation method of the said catalysts is one of the following solid phase doping technologies, or a combination of two or more such technologies.

The purpose of the following catalyst preparation is to improve the dispersion of the metal element in the silicon-based materials, and to dope the metal element effectively in the lattice of amorphous-molten-state materials made from Si bonded with one or more of C, N, and O element.

The said solid phase doping technologies include the following:

The preparation methods of metal lattice-doped silicon-based catalysts include the following solid phase doping technologies, such as Chemical Vapor Deposition (CVD), Vapor phase Axial Deposition (VAD), Laser induced Chemical Vapor Deposition (LCVD), doped sol-gel method, porous Si compound impregnation method.

Chemical Vapor Deposition (CVD): under the specific temperature (1100-2000° C.) and vacuum ($10^{-4}$ Pa-$10^4$ Pa), the silicon-based catalysts with metal dopants are obtained by the following procedures: 1) the mixture of silicon vapor or $SiCl_4$ together with metallic vapor or volatile metal salt (i.e. one or more of metal carbonyls, metal alkoxides of C atom number from 1 to 5, and organic acid salts of C atom number from 1 to 5) carried in carrier gas (i.e. one or more of $N_2$, He, $H_2$, Ar and Ke) reacts with water vapor; 2) then the products from the procedure 1) are melted in air, inert gas, or vacuum; 3) finally the products from the procedure 2) are solidified to obtain the target catalysts.

Vapor Phase Axial Deposition (VAD): under the specific temperature (1100-2000° C.) and vacuum ($10^{-4}$ Pa-$10^4$ Pa), the silicon-based catalysts with metal dopants are obtained by the following procedure: 1) the mixture of silicon vapor or $SiCl_4$ together with metallic vapor or volatile metal salt (i.e. one or more of metal carbonyls, metal alkoxides of C atom number from 1 to 5, and organic acid salts of C atom number from 1 to 5) carried in $H_2$ reacts with water vapor; 2) then the products from the procedure 1) are deposited on the surface of a high temperature device (i.e. one or more of corundum, silicon carbide, silicon nitride). The temperature of the device is controlled at a certain point between 500 and 1300° C.; 3) furthermore, the $SOCl_2$ gas is passed through for dehydrating and drying; 4) then the products from the procedure 3) are melted in air, inert gas, or vacuum; 5) the products from the procedure 4) are solidified to obtain the target catalysts.

Laser Induced Chemical Vapor Deposition (LCVD): using laser as the heat source, a technology-enhanced CVD is achieved by laser activation. Under the specific temperature (1100-2000° C.) and vacuum ($10^{-4}$ Pa-$10^4$ Pa), the silicon-based catalysts with metal dopants are obtained by following procedure: 1) the mixture of silicon vapor or $SiCl_4$ together with metallic vapor or volatile metal salt (i.e. one or more of metal carbonyls, metal alkoxides of C atom number from 1 to 5, and organic acid salts of C atom number from 1 to 5) carried in carrier gas (i.e. one or more of $N_2$, He, $H_2$, Ar, and Ke) reacts with water vapor; 2) then the products from the procedure 1) are melted in air, inert gas, or vacuum; 3) finally the products from the procedure 2) are solidified to obtain the target catalysts.

Doped sol-gel method: The liquid silicon source and organic or inorganic metal salt (such as one or more of nitrates, halides, sulfates, carbonates, hydroxides, organic acid salts of C atom number from 1 to 10, and metal alkoxides of C atom number from 1 to 10) are used as precursors, which are dissolved in a mixture of water and ethanol (the weight content of water in the mixture is 10-100%.). After the hydrolysis and condensation of the precursors, a stable transparent sol system is formed from the above-mentioned solution. After aging the sol, a three-dimensional network structure of the gel is formed slowly by the polymerization between sol particles. After drying, melting in air, in inert gas or under vacuum and then being solidified, the target catalysts are obtained.

Porous Si-based materials impregnation method: Using a porous solid silicon-based material (such as one or more of silica, silicon carbide, and silicon nitride) as a catalyst support, the support is impregnated in the solution of metal salt for metal loading. After the impregnation, the slurry is dried. The resulting powder is melted in air, in inert gas or under vacuum and then solidified, the target catalysts are obtained.

The preparation methods of the said catalysts include an important melting process, which includes a melting step such as high-temperature air melting process, high-temperature inert gas melting process, or high-temperature vacuum melting process. The preferable temperature of the melting process is 1300-2200° C.

Preferably, the inert gas in the high-temperature inert gas melting process includes one or more of $N_2$, He, Ar, and Ke.

The melting time is preferably 2-10 hrs.

The vacuum in high-temperature vacuum melting process is preferably 0.01-100 Pa.

The aim of the melting process is to dope the metal element in the silicon-based materials, and to effectively remove the introduced —OH groups of the preparation process.

Preferably, the said solidification is that the catalyst preparation involves an important cooling process after the melting process; and the said cooling process includes rapid cooling or natural cooling.

The said rapid cooling process includes one or more process of gas cooling, water cooling, oil cooling and liquid nitrogen cooling. The rate of the rapid cooling process is preferably 50-800° C./s.

Preferably, the type of oil in the said oil cooling process includes one or more of mineral oil (saturated hydrocarbon content of 50-95%, S content of ≤0.03%, a viscosity index (VI) of 80 to 170), rapeseed oil, silicone oil, PAO (poly-α olefin). The type of gas in the said gas cooling process includes one or more of inert gas (He, Ne, Ar, Ke), $N_2$ and air.

After being melted and solidified, the amorphous molten state catalysts involve an important step of grinding or molding process.

The particle size after being ground is preferably 10 nm-10 cm.

The said molding process is that the amorphous-molten-state catalysts being melted are manufactured to obtain the specific shape (such as, honeycomb-shaped monolithic catalyst, etc.) for meeting various reaction processes, or directly manufactured into tubular reactor (without addition of a catalyst).

The said catalysts that has metal dopants in one or more amorphous-molten-state materials made from Si bonded with one or more of C, N and O element can be expressed A@$SiO_2$, A@SiC, A@$Si_3N_4$, A@$SiC_xO_y$ (4x+2y=4), A@$SiO_yN_z$ (2y+3z=4), A@$SiC_xN_z$ (4x+3z=4), A@$SiC_xO_yN_z$ (4x+2y+3z=4; x, y and z are not simultaneously equal to zero), and the range of x, y and z are 0-1, 0-2, and 0-4/3, respectively. "A" denotes the metal dopants.

In A@$SiO_2$, by partially replacing Si atoms, the metal element A is inserted in the lattice of silica (Si), and bonds with the adjacent O atoms (A-O). In A@SiC catalysts, by partially replacing Si atoms, the metal element A is inserted in the lattice of silicon carbide (SiC), and bonds with the adjacent C or Si atoms (A-C or Si-A). In A@$Si_3N_4$, by partially replacing Si atoms, the metal element A is inserted the lattice of silicon nitride ($Si_3N_4$), and bonds with the adjacent N atoms (A-N). In A@$SiC_xO_y$, by partially replacing Si or C atoms, the metal element A is inserted the lattice of $SiC_xO_y$, and bonds with the adjacent C, O or Si atoms (A-C, A-O or A-Si). In A@$SiO_yN_z$, by partially replacing Si or N atoms, the metal element A is inserted the lattice of $SiO_yN_z$, and bonds with the adjacent N, O or Si atoms (A-N, A-O or A-Si). In A@$SiC_xN_z$, by partially replacing Si or C atoms, the metal element A is inserted in the lattice of $SiC_xN_z$, and bonds with the adjacent C, N or Si atoms (A-C, A-N or A-Si). In A@$SiC_xO_yN_z$, by partially replacing Si, N or C atoms, the metal element A is inserted in the lattice of $SiC_xO_yN_z$, and bonds with the adjacent C, N, O or Si atoms (A-C, A-O, A-N or A-Si). The present invention involves a method of olefins synthesis by oxygen-free direct conversion of methane, which includes three reaction modes, i.e., fluidized bed mode, moving bed mode, and fixed bed mode.

The present invention involves a method of olefins synthesis by oxygen-free direct conversion of methane, of which the feed gas includes one or more of inert and non-inert gas besides methane. With a volume content of 0~95%, the inert gas includes one or two of nitrogen ($N_2$), helium (He), neon (Ne), argon (Ar), and krypton (Ke). The non-inert gas includes one or two of carbon monoxide (CO), hydrogen ($H_2$), carbon dioxide ($CO_2$), water ($H_2O$), monohydric alcohol (the number of carbon atom is from 1 to 5), dihydric alcohol (the number of carbon atom is from 2 to 5), alkanes (the number of carbon atom is from 2 to 8); the volume ratio of non-inert gas to methane is 0~15% and the volume content of methane in the feed gas is 5~100%.

The present invention involves a method of olefins synthesis by oxygen-free direct conversion of methane, of which a pretreatment to the catalysts before the reaction is necessary. The atmosphere of the pretreatment process is feed gas or hydrocarbons and their derivatives, which contains one or a mixture from alkanes of carbon atom number from 2 to 10, alkenes of carbon atom number from 2 to 10, alkyne of carbon atom number from 2 to 10, monohydric alcohol of carbon atom number from 1 to 10, dihydric alcohol of carbon atom number from 2 to 10, aldehyde of carbon atom number from 1 to 10, carboxylic acid of carbon atom number from 1 to 10, aromatics of carbon atom number from 6 to 10. Pretreatment temperature is 800~1000° C.; pretreatment pressure is under 0.1~1 Mpa, preferably atmospheric pressure. The weight hourly space velocity of feed gas is 500~3000 ml/g/h, preferably 800~2400 ml/g/h.

The present invention involves a method of olefins synthesis by oxygen-free direct conversion of methane, of which the reaction process includes continuous flow reaction mode or batch reaction mode. Under the continuous flow reaction mode, the reaction temperature is 750-1200° C., preferably 800-1150° C.; the reaction pressure is under 0.1~1 MPa, preferably atmospheric pressure; the weight hourly space velocity of feed gas is 1000~30000 ml/g/h, and preferably 4000~20000 ml/g/h. Under the batch reaction mode, the reaction pressure is preferably 1-20 MPa; the reaction time is preferably ≥5 min.

The present invention involves a method of olefins synthesis by oxygen-free direct conversion of methane, which the olefin products include one or two of ethylene, propylene, or butylene, and the joint products in the reaction include aromatics and hydrogen. The aromatic products include one or more of benzene, toluene, xylene, o-xylene, m-xylene, ethylbenzene, and naphthalene.

Based on the research of the methane dehydroaromatization process, this invention discloses a metal doped silicon-based catalyst for olefins, aromatics and hydrogen production by direct conversion of methane under oxygen-free and continuous flow reaction mode. Compared with the previous oxygen-free methane conversion process, this method has the following characteristics:

1. Reaction process
1) High olefin selectivity (30-90%);
2) The selectivity of the aromatic co-products is achieved to 10-70%;
3) Other than a little coke deposition in the initial, the follow-up reaction process presents zero coke deposition;
4) The products can be easily separated.

2. Catalysts
1) Simple preparation method and low cost;
2) High mechanical strength and good thermal conductivity;
3) microporous or mesoporous materials not necessary;
4) Fabricating arbitrarily different shapes and specifications according to reaction conditions and reaction processes;
5) High stability under the atmosphere of redox and hydrothermal condition at 800~1150° C.;
6) Long catalyst life (>100 hrs) due to zero coke deposition and unique structure of the catalyst.

In summary, the said reaction process has many advantages, such as long life of catalysts, high stability, high selectivity of target products, zero coke deposition, easy separation of products, good reproducibility, safe and reliable operation and among others, which are very important for industrial application.

Although it seems that there are some similarities in the products distribution between the present invention and the methane dehydroaromatization, there are fundamental differences, such as in catalysts and reaction mechanism. Firstly, a microporous zeolite support is necessary for methane dehydroaromatization process. Secondly, the current accepted reaction mechanism for methane dehydroaromatization is shown in Scheme 1. Methane is dissociated on the surface of the resulting active sites (such as $MoC_x$, WC, Re) to produce $CH_x$ species; subsequently, $CH_x$ species are coupled on the surface of zeolite supported catalyst to form the $C_2H_y$ species; then $C_2H_y$ species is coupled and cyclized on the Brønsted acidic sites of the zeolite, in which aromatics is formed by the shape selectivity of zeolite channel. (J. Energy Chem. 2013, 22, 1-20)

Scheme 1 the reaction mechanism of the methane dehydroaromatization over $MoC_x$/Zeolite catalyst.

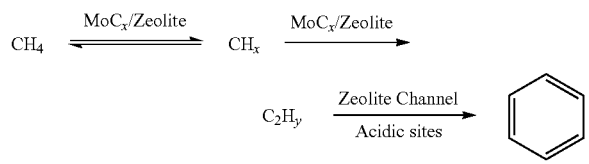

However, the catalysts of the present patent are that metal elements doped in the lattice of materials with amorphous molten state made from Si bonded with one or more of C, N and O element. The reaction mechanism is that methane is induced by the active species (dopant metal in the lattice) to produce $\cdot CH_3$ radicals, which are further coupled and dehydrogenated to obtain the olefins, aromatics and hydrogen (Scheme 2).

Scheme 2 the radical mechanism of the methane dehydroaromatization over $A@SiO_xC_yN_z$ catalyst.

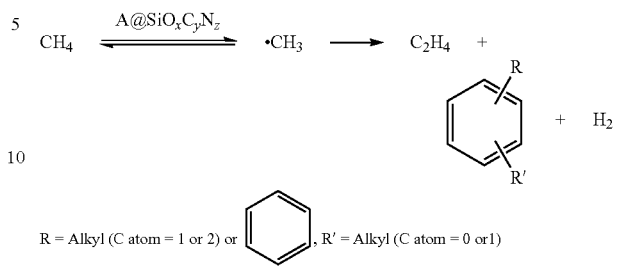

The differences between the present invention and the methane dehydroaromatization are as follows: 1) it is necessary for the methane dehydroaromatization to possess channels of zeolite with specific size and structure, as well as acidic sites of zeolite with certain amount and type. Whereas the catalysts in the present patent are amorphous molten state materials without channel and acid; 2) the mechanism of methane dehydroaromatization is a synergistic interaction between active Mo species and acidic sites of zeolite, while the present patent is a radical induction mechanism.

In the present patent, the methane conversion is 8-50%; olefin selectivity is 30-90%; aromatic selectivity is 10-70%. The said reaction process using the claimed catalysts has many advantages, such as long life of catalysts (>100 hrs), high stability of redox and hydrothermal conditions in high temperature, high selectivity of target products, zero coke deposition, easy separation of products, good reproducibility, safe and reliable operation and among others, which are very desirable for industrial application.

EMBODIMENTS

1. Catalyst Preparation

Figure 1:
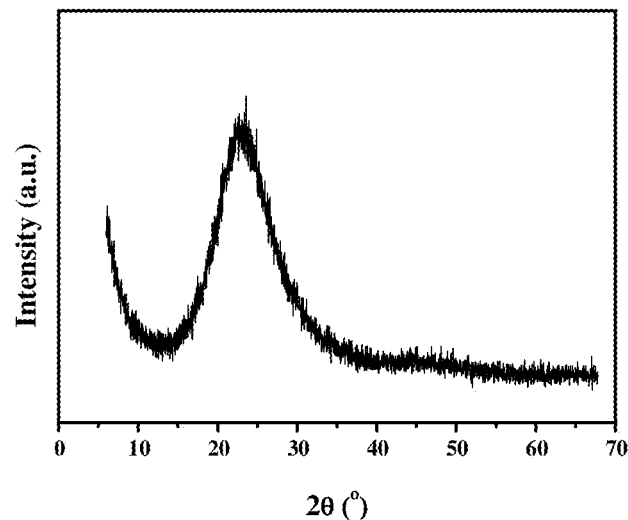
FIG. 1 XRD pattern of 0.5 wt. % Ca-0.5 wt. % Fe $@SiO_2$ catalyst
FIG. 2 XPS spectra of Fe doping 6H—SiC(0001)
FIG. 3 HRTEM image of the metal lattice-doping catalyst

The preparation methods of silicon-based catalysts with metal dopants include the following solid phase doping technologies, such as Chemical Vapor Deposition (CVD), Vapour phase Axial Deposition (VAD), Laser induced Chemical Vapor Deposition (LCVD), metal doping sol-gel method, porous Si-based materials impregnation method, powder doping method and so on. The catalysts are marked as: $A@SiO_xC_yN_z$.

The preparation of $A@SiO_2$ catalysts (example 1, 2, 3, 4, 5, 7); the preparation of $A@SiOC_{0.5}$ catalysts (example 6); the preparation of $A@Si_3C_4$ catalysts (example 8, 9, 10); the preparation of $A@Si_3N_4$ catalysts (example 11); the preparation of $A@SiOC_{0.35}N_{0.2}$ catalysts (example 12); the preparation of $A/SiO_2$ catalysts (example 13) (Active species is highly dispersed on the support.)

Example 1

Chemical Vapor Deposition (CVD)
The vapor phase in the high-temperature reaction furnace is formed by bubbling 30 mL/min of carrier gas (10 vol. % of $H_2$ and 90 vol. % of He) into an 30 mL of ethanol solution dissolving 17 g of $SiCl_4$ and 94 mg of $Co_2(CO)_8$. The mist vapor mixture sprayed from the center of combustor is hydrolyzed and melted to form a uniform $SiO_2$ material doped with Co at 1200° C. The material is melted at 1400° C. in vacuum (10 Pa) for 6 h. The Co doped silica catalyst, 0.5 wt. % Co@$SiO_2$, is obtained after subsequent quenching in cold water.

Example 2

Chemical Vapor Deposition (CVD)

The vapor phase in the high-temperature reaction furnace is formed by bubbling 30 mL/min of carrier gas (10 vol. % of $H_2$ and 90 vol. % of He) into an 30 mL of ethanol solution dissolving 17 g of $SiCl_4$, 94 mg of $Co_2(CO)_8$ and 86.9 mg $Ni(CO)_4$. The mist vapor mixture sprayed from the center of combustor is hydrolyzed and melted at 1200° C. to form a uniform $SiO_2$ material doped with Co and Ni. The material is further melted at 1400° C. in vacuum (10 Pa) for 6 h. The Co/Ni doping silica catalyst, 0.5 wt. % Co-0.5 wt. % Ni@$SiO_2$, is obtained after subsequent quenching in cold water.

Example 3

Vapor Phase Axial Deposition (VAD)

The vapor phase in the high-temperature reaction furnace is formed by bubbling 30 mL/min of carrier gas (10 vol. % of $H_2$ and 90 vol. % of He) into an 30 mL of ethanol solution dissolving 17 g of $SiCl_4$, 94 mg of $Co_2(CO)_8$. The mist vapor mixture sprayed from the center of combustor is hydrolyzed and axial deposited on the surface of alumina support at 1200° C. to form a uniform $SiO_2$ material doped with Co. The material is melted at 1400° C. in vacuum (10 Pa) for 6 h. The Co doping silica catalyst, 0.5 wt. % Co@$SiO_2$, is obtained after subsequent quenching in cold water.

Example 4

Vapor Phase Axial Deposition (VAD)

The vapor phase in the high-temperature reaction furnace is formed by bubbling 30 mL/min of carrier gas (10 vol. % of $H_2$ and 90 vol. % of He) into an 30 mL of ethanol solution dissolving 17 g of $SiCl_4$, 94 mg of $Co_2(CO)_8$ and 86.9 mg $Ni(CO)_4$. The mist vapor mixture sprayed from the center of combustor is hydrolyzed and axial deposited on the surface of alumina support at 1200° C. to form a uniform $SiO_2$ material doped with Co and Ni. The obtained material is melted at 1400° C. in vacuum (10 Pa) for 6 h. The Co doping silica catalyst, 0.5 wt. % Co-0.5 wt. % Ni@$SiO_2$, is obtained after subsequent quenching in cold water.

Example 5

Metal Doping Sol-Gel Method A metal doping silica gel is formed by stirring 20 mL of tetraethoxysilane (TEOS), 120 mg of $Co(NO_3)_2 \cdot 6H_2O$, 117.1 mg $Ca(NO_3)_2 \cdot 4H_2O$ and 30 mL ethanol in 24 g 15% nitric acid solution at 60° C. for 24 h. The gel is dried in rotary evaporator at 80° C. for 2 h and melted at 1400° C. in He atmosphere for 6 h. The Co/Ca doped silica catalyst, 0.5 wt. % Ca-0.5 wt. % Co@$SiO_2$, is obtained after subsequent quenching in cold water.

Example 6

The vapor phase in the high-temperature reaction furnace is formed by bubbling 30 mL/min of carrier gas (10% v of $H_2$ and 90% v of He) into an 30 mL of ethanol solution dissolving 17 g of $SiCl_4$ and 94 mg of $Co_2(CO)_8$. The mist vapor mixture sprayed from the center of combustor is hydrolyzed and melted at 1200° C. to form a uniform $SiO_2$ material doped with Co. The material is treated in a mixed gas (10% v of $CH_4$ and 90% v of He) at 2000° C. and afterwards melted at 1400° C. in vacuum (10 Pa) for 6 h. The Co doped catalyst, 0.5 wt. % Co@$SiOC_{0.5}$, is obtained after subsequent quenching in cold water.

Example 7

Porous Si-Based Materials Impregnation Method

The catalyst is prepared by impregnating 6 g of porous silica powder in a solution of 117 mg of $Ca(NO_3)_2 \cdot 4H_2O$ and 137.3 mg of $Co(NO_3)_2 \cdot 6H_2O$ in 10 mL of water. The slurry is dried by stirring and aging for 24 h at 120° C. and afterwards melted at 1400° C. in vacuum (10 Pa) for 6 h. The Co/Ca doped catalyst, 0.5 wt. % Ca-0.5 wt. % Co@$SiO_2$, is obtained after subsequent melting process at 1400° C. in vacuum (10 Pa) for 6 h.

Example 8

Porous Si-Based Materials Impregnation Method

The metal doped is prepared by impregnating 6 g of porous silicon carbide powder in a solution of 216 mg of $Fe(NO_3)_3 \cdot 9H_2O$ in 10 mL of water. The slurry is dried by stirring and aging for 24 h at 120° C. The dry powder is melted at 2000° C. in vacuum (10 Pa) for 6 h to form a uniform SiC material doped with Fe. The Fe doping catalyst, 0.5 wt. % Fe@SiC, is obtained after subsequent quenching in rapeseed oil.

Example 9

A metal doped silica gel is formed by stirring 20 mL of tetraethoxysilane (TEOS), 120 mg of $Co(NO_3)_2 \cdot 6H_2O$, 117.1 mg $Ca(NO_3)_2 \cdot 4H_2O$ and 30 mL ethanol in 24 g 15% nitric acid solution at 60° C. for 24 h. The gel is dried in rotary evaporator at 80° C. for 2 h and melted with carbon at 2000° C. for 2.5 h to form a uniform SiC material doped with Co and Ca. The Co/Ca doping silica catalyst, 0.5 wt. % Ca-0.5 wt. % Co@$SiOC_{0.5}$, is obtained after subsequent quenching in cold water.

Example 10

A metal doped silica gel is formed by stirring 20 mL of tetraethoxysilane (TEOS), 120 mg of $Co(NO_3)_2 \cdot 6H_2O$, 117.1 mg $Ca(NO_3)_2 \cdot 4H_2O$ and 30 mL ethanol in 24 g 15% nitric acid solution at 60° C. for 24 h. The gel is dried in rotary evaporator at 80° C. for 2 h and calcined with carbon at 2000° C. for 12 h to form a uniform SiC material doped with Co and Ca. The Co/Ca doping silica catalyst, 0.5 wt. % Ca-0.5 wt. % Co@SiC, is obtained after subsequent quenching in cold water.

Example 11

The catalyst (0.5 wt. % Ca-0.5 wt. % Co@$SiO_2$) mentioned in example 5 is treated in nitriding furnace at 1150-1200° C. at $NH_3$ atmosphere for 4 h and then 1350-1450° C. at $NH_3$ atmosphere for 18-36 h, until all become far nitride to form a uniform $Si_3N_4$ material doped with Co and Ca. The resulting powder is 0.5 wt. % Ca-0.5 wt. % Co@$Si_3N_4$.

Example 12

The catalyst (0.5 wt. % Co@SiOC$_{0.5}$) mentioned in example 6 is treated in nitriding furnace at 1150-1200° C. at NH$_3$ atmosphere for 4 h and then 1350-1450° C. at NH$_3$ atmosphere for 7.5 h to form a uniform SiOC$_{0.35}$N$_{0.3}$ material doped with Co. The resulting powder is 0.5 wt. % Ca-0.5 wt. % Co@SiOC$_{0.35}$N$_{0.3}$.

Example 13

The metal loading catalyst is prepared by impregnating 6 g of silica support in a solution of 94 mg of Co$_2$(CO)$_8$ in 10 mL of water. The slurry is stirred vigorously for 12 h and aging for 24 h at 60° C. The Co loading catalyst, 0.5 wt. % Co/SiO$_2$, is obtained after subsequent calcination at 550° C. in air for 6 h.

For the further understanding of the invention, the following examples are given for purpose of illustration only and should not be regarded as limiting in any way.

2. Catalyst Characterization a) XRD Characterization of 0.5 wt. % Ca-0.5 wt. % Fe @SiO$_2$ Catalyst The XRD pattern of the catalyst indicates that there is only a broad diffraction peak at 23°, which shows an amorphous characteristic peak of SiO$_2$ (FIG. 1). Meanwhile, the diffraction peaks of Fe and Ca cannot be observed. All of these results are significantly different from the zeolite catalyst system.

b) Inductively Coupled Plasma Atomic Emission Spectrometry (ICP-AES) Leaching Characterization The so-called ICP-AES acid leaching method is that the metal atoms outside the Si-based support can be dissolved in dilute nitric acid (The dilute nitric acid can only dissolves the metal, but it cannot dissolve the supports), while those protected by the Si-based support lattice or Si-based support cannot be dissolved, and meanwhile the ICP-ASE results can obtain a degree of acid leaching (i.e., a ratio of surface loadings to surface loading and doping loading). Firstly, the 0.5 wt. % Co@SiO$_2$ catalyst was leached by dilute nitric acid, and the results showed that no Co atoms can be detected by ICP-AES, and further revealed the Co atoms have inserted the lattice of Si-based support. Subsequently, the 0.5 wt. % Co@SiO$_2$ catalyst was leached by HF acid (the HF acid can dissolve either metal atoms or Si-based support), the results showed that all of Co atoms can be detected by ICP-AES, and the leaching amount is equal to the loading amount of the Co@SiO$_2$ catalyst. The above results show that all of Co atoms have been inserted inside the lattice of Si-based support, and almost no Co atoms can be detected on the surface of Si-based support.

c) XPS Characterization of Fe-Doped 6H—SiC(0001)

Figure 2:
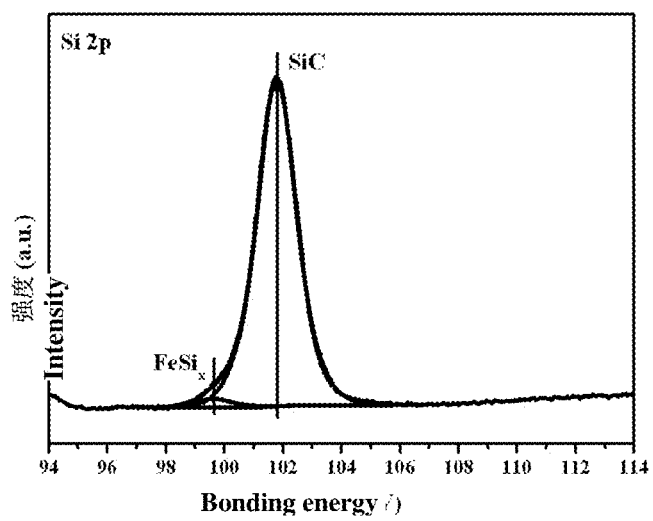

As can be seen from the result of XPS Si2p (FIG. 2), there is an obvious shoulder peak at the binding energy of 99.6 eV, which attributes to the FeSi$_x$ species. Furthermore, the results show Fe atom could substitute the lattice C atoms, and then the Fe atoms could bond with Si atom to form the FeSi$_x$ species.

d) ICP-AES Leaching Characterization of 0.5 wt. % Co/SiO$_2$ Catalyst

Figure 3:
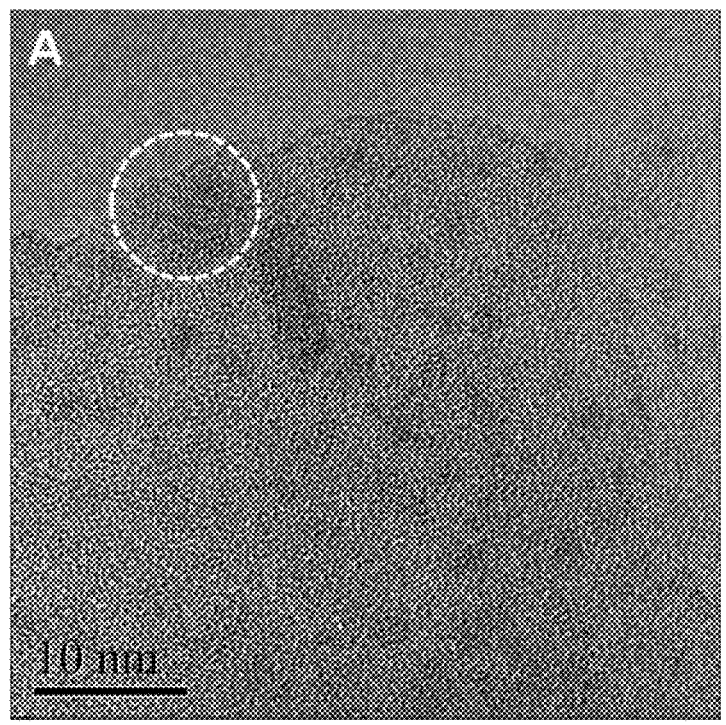
Figure 3:
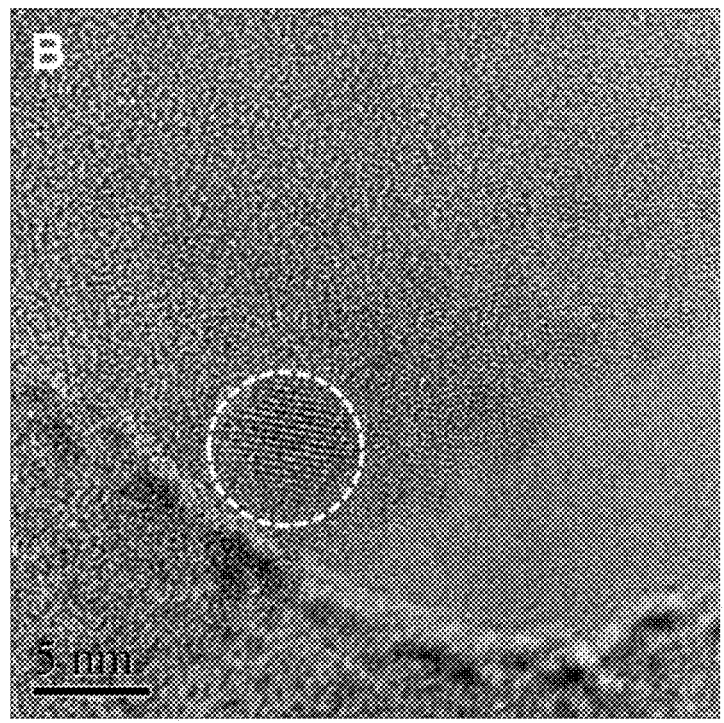

Firstly, the 0.5 wt. % Co@SiO$_2$ catalyst was leached by dilute nitric acid, and the results showed that all of Co atoms can be detected by ICP-AES, and the leaching amount is equal to the catalyst loading amount. Furthermore, the results show that all of Co atoms have dispersed on the surface of Si-based support, and almost no Co atoms can be inserted inside the lattice of Si-based support.

e) High Resolution Transimission Microscopy (HR-TEM) Image of the Metal Lattice-Doping Catalyst Furthermore, HR-TEM was used to characterize the dispersion and configuration of the metal lattice-doping catalyst prepared by the metal doping sol-gel method (Example 5 of catalyst preparation), FIG. 3. As can be seen from this image, we can observe a clear crystal structure (white circles), FIGS. 3A and 3B. The HR-TEM results prove that the so-called amorphous molten state catalysts exhibited the structure with long-range disorder and short-range order.

3. Under the Oxygen-Free and Continuous Flow Conditions, Methane is Directly Converted to Olefin, Aromatics and Hydrogen.

All of the above catalyst prior to use need to be ground and sieved to 20-30 mesh as a backup.

All of the following reaction examples are achieved in a continuous flow micro-reaction apparatus, which is equipped with gas mass flow meters, gas deoxy and dehydration units, and online product analysis chromatography. The tail gas of reaction apparatus is connected with the metering valve of chromatography, and thus periodic and real-time sampling and analysis will be achieved. The feed gas is composed of 10 vol. % N$_2$ and 90 vol. % CH$_4$ without specification, in which the nitrogen (N$_2$) is used in an internal standard. To achieve the online product analysis, the Agilent 7890A chromatography with dual detector of FID and TCD is used. The FID detector with HP-1 capillary column is used to analyze the light olefin, light alkane and aromatics; and the TCD detector with Hayesep D packed column is used to analyze the light olefin, light alkane, methane, hydrogen and N$_2$ internal standard. According to the carbon balance before and after reaction, methane conversion, product selectivity and coke deposition selectivity are calculated by the method from the two Chinese patents (CN1247103A, CN1532546A).

Example 1

The 0.75 g 0.5 wt. % Co@SiO$_2$ catalyst prepared by the Example 1 of catalyst preparation method was loaded in the fix-bed reactor, and then purged by Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas was adjusted to 4840 ml/g/h. After the WHSV being kept 20 mins, the reaction results were analyzed by the online chromatography. The results were as follows: 8.2% of methane conversion, 47.6% and 1.0 µmol/g$_{catalyst}$/s of ethylene selectivity and ethylene generation rate, 26.1% and 0.2 µmol/g$_{catalyst}$/s of benzene selectivity and benzene generation rate, 26.2% and 0.1 µmol/g$_{catalyst}$/s of Naphthalene selectivity and Naphthalene generation rate, and 5.4 µmol/g$_{catalyst}$/s of hydrogen generation rate.

Examples 2-7

The 0.75 g 0.5 wt. % Co@SiO$_2$ catalyst prepared by the Examples 2-7 of catalyst preparation method was loaded in the fix-bed reactor, and then purged by Ar gas (25 ml/min) for 20 mins. Maintaining a constant flow rate of Ar, the reactor is programmed from room temperature up to the following temperatures (Table 1) at a heating rate of 10° C./min. And then the weight hourly space velocity (WHSV) of feed gas was adjusted according to following values (Table 1). The results of methane conversion and products selectivity are as follows:

TABLE 1

| Example | Temp.[1] (° C.) | WHSV[2] (ml/g/h) | Methane Conv.[3] (%) | Ethylene Sel.[4] (%) | Benzene Sel. (%) | Naphthalene Sel. (%) |
|---|---|---|---|---|---|---|
| 2 | 750 | 1600 | 2.5 | 70 | 16 | 14 |
| 3 | 850 | 2200 | 5.6 | 65 | 20 | 15 |
| 4 | 900 | 3600 | 6.4 | 55 | 22 | 23 |
| 5 | 950 | 5100 | 7.9 | 52 | 23 | 25 |
| 6 | 980 | 8400 | 15.2 | 48 | 24 | 28 |
| 7 | 1050 | 15200 | 9.8 | 46 | 25 | 29 |

[1]Temp. denotes temperature;
[2]WHSV denotes the weight hourly space velocity;
[3]Conv. denotes conversion;
[4]Sel. Denotes selectivity.

Example 8

The 1.5 g 0.5 wt. % Ca-0.5 wt. % Co@SiC catalyst prepared by Example 10 of the catalyst preparation method was loaded in the fix-bed reactor, and then purged by Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas was adjusted to 4840 ml/g/h. After the WHSV being kept 20 mins, the reaction results were analyzed by the online chromatography. The results were as follows: 8.02% of methane conversion, 46.4% and 1.2 $\mu mol/g_{catalyst}/s$ of ethylene selectivity and ethylene generation rate, 26.2% and 0.2 $\mu mol/g_{catalyst}/s$ of benzene selectivity and benzene generation rate, 27.3% and 0.1 $\mu mol/g_{catalyst}/s$ of Naphthalene selectivity and Naphthalene generation rate, and 6.4 $\mu mol/g_{catalyst}/s$ of hydrogen generation rate.

Examples 9-13

The 1.5 g 0.5 wt. % Ni-0.5 wt. % Co@SiO$_2$ catalyst prepared by Example 4 of the catalyst preparation method was loaded in the fix-bed reactor, and then purged by Ar gas (25 ml/min) for 20 mins. Maintaining a constant flow rate of Ar, the reactor is programmed from room temperature up to following temperatures (Table 1) at a heating rate of 10° C./min. And then the weight hourly space velocity (WHSV) of feed gas was adjusted to following value (Table 2). The results of methane conversion and products selectivity were as follows:

TABLE 2

| Example | Temp.[1] (° C.) | WHSV[2] (ml/g/h) | Methane Conv.[3] (%) | Ethylene Sel.[4] (%) | Benzene Sel. (%) | Naphthalene Sel. (%) |
|---|---|---|---|---|---|---|
| 9 | 750 | 1600 | 2.2 | 68 | 16 | 16 |
| 10 | 850 | 2200 | 5.9 | 62 | 23 | 15 |
| 11 | 900 | 3600 | 6.8 | 51 | 24 | 25 |
| 12 | 950 | 5100 | 7.5 | 50 | 25 | 25 |
| 13 | 980 | 8400 | 14.3 | 49 | 23 | 28 |

[1]Temp. denotes temperature;
[2]WHSV denotes the weight hourly space velocity;
[3]Conv. denotes conversion;
[4]Sel. Denotes selectivity.

Example 14

The 0.75 g 0.5 wt. % Ca-0.3 wt. % Al@SiO$_2$ catalyst prepared by Example 5 of catalyst preparation method was loaded in the fix-bed reactor, and then purged by Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas was adjusted to 4840 ml/g/h. After the WHSV being kept 20 mins, the reaction results were analyzed by the online chromatography. After 100 hours, the results were as follows: 7.8% of methane conversion, 46.8% and 0.9 $\mu mol/g_{catalyst}/s$ of ethylene selectivity and ethylene generation rate, 27.2% and 0.2 $\mu mol/g_{catalyst}/s$ of benzene selectivity and benzene generation rate, 25.8% and 0.1 $\mu mol/g_{catalyst}/s$ of Naphthalene selectivity and Naphthalene generation rate, and 5.2 $\mu mol/g_{catalyst}/s$ hydrogen generation rate.

Example 15

The 0.75 g 0.5 wt. % Co@SiOC$_{0.5}$ catalyst prepared by Example 6 of catalyst preparation method was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. And then the weight hourly space velocity (WHSV) of feed gas was adjusted to 4840 ml/g/h. After the WHSV being kept 20 mins, the reaction results were analyzed by the online chromatography. The results were as follows: 8.2% of methane conversion, 47.3% and 1.2 $\mu mol/g_{catalyst}/s$ of ethylene selectivity and ethylene generation rate, 22.0% and 0.23 $\mu mol/g_{catalyst}/s$ of benzene selectivity and benzene generation rate, 29.2% and 0.14 $\mu mol/g_{catalyst}/s$ of Naphthalene selectivity and Naphthalene generation rate, and 6.4 $\mu mol/g_{catalyst}/s$ of hydrogen generation rate.

Examples 16-19

The 0.75 g 0.5 wt. % Co@SiOC$_{0.5}$ catalyst prepared by Example 6 of the catalyst preparation method was loaded in the fix-bed reactor, and then purged by Ar gas (25 ml/min) for 20 mins. Maintaining a constant flow rate of Ar, the reactor was programmed from room temperature up to following temperature (Table 1) at a heating rate of 10° C./min. And then the weight hourly space velocity (WHSV) of feed gas was adjusted to following value (Table 3). The results of methane conversion and products selectivity were as follows:

TABLE 3

| Example | Temp.[1] (° C.) | WHSV[2] (ml/g/h) | Methane Conv.[3] (%) | Ethylene Sel.[4] (%) | Benzene Sel. (%) | Naphthalene Sel. (%) |
|---|---|---|---|---|---|---|
| 16 | 750 | 1600 | 3.0 | 72 | 12 | 16 |
| 17 | 850 | 2200 | 5.3 | 64 | 21 | 15 |
| 18 | 900 | 3600 | 7.1 | 53 | 24 | 23 |
| 19 | 950 | 5100 | 7.9 | 47 | 25 | 28 |
| 20 | 980 | 8400 | 15.5 | 45 | 23 | 32 |

[1]Temp. denotes temperature;
[2]WHSV denotes the weight hourly space velocity;
[3]Conv. denotes conversion;
[4]Sel. Denotes selectivity.

Example 21

The 0.75 g 0.5 wt. % Ca-0.3 wt. % Zn@SiOC$_{0.5}$ catalyst prepared by Example 6 of the catalyst preparation method was loaded in the fix-bed reactor, and then purged by Ar gas (25 ml/min) for 20 mins. Maintaining a constant flow rate of Ar, the reactor was programmed from room temperature up to 1000° C. at a heating rate of 10° C./min. And then the weight hourly space velocity (WHSV) of feed gas was adjusted to 10000 ml/g/h. After the WHSV being kept 20 mins, the reaction results were analyzed by the online chromatography. The results were as follows: 31% of methane conversion, 52.1% and 5.7 $\mu mol/g_{catalyst}/s$ of ethylene selectivity and ethylene generation rate, 21.3% and 0.8 $\mu mol/g_{catalyst}/s$ of benzene selectivity and benzene generation rate, 26.4% and 0.6 $\mu mol/g_{catalyst}/s$ of Naphthalene selectivity and Naphthalene generation rate, and 28 $\mu mol/g_{catalyst}/s$ of hydrogen generation rate.

Example 22

The 0.75 g 0.5 wt. % Ca-0.3 wt. % Co@SiOC$_{0.5}$ catalyst prepared by the Example 9 of catalyst preparation method was loaded in the fix-bed reactor, and then purged with the Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas (10 vol. % CH$_4$, 5 vol. % N$_2$ and 85 vol. % He) was adjusted to 4840 ml/g/h. After the WHSV being kept 20 mins, the reaction results were analyzed by the online chromatography. The results were as follows: 7.1% of methane conversion, 51.3% and 0.1 $\mu mol/g_{catalyst}/s$ of ethylene selectivity and ethylene generation rate, 14.3% and 0.01 $\mu mol/g_{catalyst}/s$ of benzene selectivity and benzene generation rate, 7.4% and 0.003 $\mu mol/g_{catalyst}/s$ of Naphthalene selectivity and Naphthalene generation rate, 26.6% of coke selectivity, and 0.5 $\mu mol/g_{catalyst}/s$ of hydrogen generation rate.

Example 23

The 0.75 g 0.5 wt. % Ca-0.6 wt. % Co@SiOC$_{0.5}$ catalyst prepared by the Example 6 of catalyst preparation method was loaded in the fix-bed reactor, and then purged with the Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas (88 vol. % CH$_4$, 2 vol. % CO, 8 vol. % N$_2$ and 2 vol. % He) was adjusted to 4840 ml/g/h. After the WHSV being kept 20 mins, the reaction results were analyzed by the online chromatography. The results were as follows: 8.5% of methane conversion, 40.4% and 0.8 $\mu mol/g_{catalyst}/s$ of ethylene selectivity and ethylene generation rate, 25.6% and 0.2 $\mu mol/g_{catalyst}/s$ of benzene selectivity and benzene generation rate, 31.4% and 0.1 $\mu mol/g_{catalyst}/s$ of Naphthalene selectivity and Naphthalene generation rate, 0.4% of coke selectivity, and 5.5 $\mu mol/g_{catalyst}/s$ of hydrogen generation rate.

Example 24

The 0.75 g 0.2 wt. % Mg-0.3 wt. % Zn@SiOC$_{0.5}$ catalyst prepared by the Example 9 of catalyst preparation method was loaded in the fix-bed reactor, and then purged with the Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas (5.4 vol. % CH$_3$OH, 85 vol. % CH$_4$ and 9.6 vol. % N$_2$) was adjusted to 4840 ml/g/h. After the WHSV being kept 20 mins, the reaction results were analyzed by the online chromatography. The results were as follows: 6% of methane conversion, 64.5% and 0.9 $\mu mol/g_{catalyst}/s$ of ethylene selectivity and ethylene generation rate, 15.1% and 0.07 $\mu mol/g_{catalyst}/s$ of benzene selectivity and benzene generation rate, 8.9% and 0.02 $\mu mol/g_{catalyst}/s$ of Naphthalene selectivity and Naphthalene generation rate, 3.6% and 0.05 $\mu mol/g_{catalyst}/s$ of ethane selectivity, 7.8% of coke selectivity, and 9.3 $\mu mol/g_{catalyst}/s$ of hydrogen generation rate.

Example 25

The 0.75 g 0.5 wt. % Ca-0.3 wt. % Co@SiOC$_{0.5}$ catalyst prepared by the Example 9 of the catalyst preparation method was loaded in the fix-bed reactor, and then purged with the Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of the feed gas (5.4 vol. % CH$_3$OH, 85 vol. % CH$_4$ and 9.6 vol. % N$_2$) was adjusted to 10000 ml/g/h. After the WHSV being kept 20 mins, the reaction results were analyzed by the online chromatography. The results were as follows: 22% of methane conversion, 60.9% and 6.6 $\mu mol/g_{catalyst}/s$ of ethylene selectivity and ethylene generation rate, 14.3% and 0.5 $\mu mol/g_{catalyst}/s$ of benzene selectivity and benzene generation rate, 7.6% and 0.2 $\mu mol/g_{catalyst}/s$ of Naphthalene selectivity and Naphthalene generation rate, 2.3% and 0.3 $\mu mol/g_{catalyst}/s$ of ethane selectivity, 14.1% of coke selectivity, and 39 $\mu mol/g_{catalyst}/s$ of hydrogen generation rate.

Example 26

The 0.75 g 0.5 wt. % Mn-1.1 wt. % Fe@SiOC$_{0.5}$ catalyst prepared by Example 6 of the catalyst preparation method was loaded in the fix-bed reactor, and then purged by Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas (5 vol. % CO$_2$, 85 vol. % CH$_4$ and 10 vol. % N$_2$) was adjusted to 4840 ml/g/h. After the WHSV being kept 20 mins, the reaction results were analyzed by the online chromatography. The results were as follows: 8.3% of methane conversion, 42.2% and 0.8 $\mu mol/g_{catalyst}/s$ of ethylene selectivity and ethylene generation rate, 25.3% and 0.2 $\mu mol/g_{catalyst}/s$ of benzene selectivity and benzene generation rate, 23.6% and 0.1 $\mu mol/g_{catalyst}/s$ of Naphthalene selectivity and Naphthalene generation rate, 3.2% and 0.06 $\mu mol/g_{catalyst}/s$ of ethane selectivity, 7.1% of coke selectivity, and 2.0 $\mu mol/g_{catalyst}/s$ of hydrogen generation rate.

Example 27

The 0.5 g 0.2 wt. % K-0.6 wt. % Fe@SiO$_2$ catalyst prepared by Example 5 of the catalyst preparation method (replacing Co(NO$_3$)$_2$.6H$_2$O and Ca(NO$_3$)$_2$.4H$_2$O with KNO$_3$ and Fe(NO$_3$)$_3$.9H$_2$O) was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. And then the weight hourly space velocity (WHSV) of feed gas was adjusted to 10800 ml/g/h. After the WHSV being kept 20 mins, the reaction results were analyzed by the online chromatography. The results were as follows: 9.8% of methane conversion, 43% of ethylene selectivity, 25% of benzene selectivity, 27% of Naphthalene selectivity, 2% of ethane selectivity, and 3% of coke selectivity.

Example 28

The 0.65 g 0.1 wt. % K-0.6 wt. % Pb@SiOC$_{0.5}$ catalyst prepared by Example 6 of the catalyst preparation method (replacing Co(NO$_3$)$_2$.6H$_2$O and Ca(NO$_3$)$_2$.4H$_2$O with KNO$_3$ and Pb(NO$_3$)$_2$) was loaded in the fix-bed reactor, and then purged by Ar gas (25 ml/min) for 20 mins. Maintaining a constant flow rate of Ar, the reactor is programmed from room temperature up to 950° C. at a heating rate of 10° C./min. And then the weight hourly space velocity (WHSV) of feed gas was adjusted to 10800 ml/g/h. After the WHSV being kept 20 mins, the reaction results were analyzed by the online chromatography. The results were as follows: 7.4% of methane conversion, 47% of ethylene selectivity, 23% of benzene selectivity, 28% of Naphthalene selectivity, and 2% of ethane selectivity.

Example 29

The 0.65 g 0.1 wt. % K-0.6 wt. % Ti@SiO$_2$ catalyst prepared by Example 5 of the catalyst preparation method (replacing Co(NO$_3$)$_2$.6H$_2$O and Ca(NO$_3$)$_2$.4H$_2$O with KNO$_3$ and tetrabutyl titanate) was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. Then the weight hourly space velocity (WHSV) of feed gas was adjusted to 10800 ml/g/h. After the WHSV being kept 20 mins, the reaction results were analyzed by the online chromatography. The results were as follows: 7.4% of methane conversion, 47% of ethylene selectivity, 23% of benzene selectivity, 28% of Naphthalene selectivity, and 2% of ethane selectivity.

Example 30

The 0.65 g 0.1 wt. % Mg-0.6 wt. % Ce@SiO$_2$ catalyst prepared by Example 5 of the catalyst preparation method (replacing Co(NO$_3$)$_2$.6H$_2$O and Ca(NO$_3$)$_2$.4H$_2$O with Mg(NO$_3$).2H$_2$O and Ce (NO$_3$)$_3$.6H$_2$O) was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. Then the weight hourly space velocity (WHSV) of feed gas was adjusted to 10800 ml/g/h. After the WHSV being kept 20 mins, the reaction results were analyzed by the online chromatography. The results were as follows: 10.2% of methane conversion, 49% of ethylene selectivity, 23% of benzene selectivity, 25% of Naphthalene selectivity, 3% of ethane selectivity, and 3% of coke selectivity.

Example 31

The 0.65 g 0.1 wt. % Mg-0.3 wt. % Sn@SiO$_2$ catalyst prepared by Example 5 of the catalyst preparation method (replacing Co(NO$_3$)$_2$.6H$_2$O and Ca(NO$_3$)$_2$.4H$_2$O with Mg(NO$_3$).2H$_2$O and SnCl$_4$.5H$_2$O) was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. Then the weight hourly space velocity (WHSV) of feed gas was adjusted to 11200 ml/g/h. After the WHSV being kept 20 mins, the reaction results were analyzed by the online chromatography. The results were as follows: 6.2% of methane conversion, 43% of ethylene selectivity, 24% of benzene selectivity, 28% of Naphthalene selectivity, 2% of ethane selectivity, and 3% of coke selectivity.

Example 32

The 0.75 g 0.5 wt. % Fe@SiC catalyst prepared by Example 5 of the catalyst preparation method was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. Then the weight hourly space velocity (WHSV) of feed gas was adjusted to 15200 ml/g/h. After the WHSV being kept 20 mins, the reaction results were analyzed by the online chromatography. The results were as follows: 12.5% of methane conversion, 44% of ethylene selectivity, 22% of benzene selectivity, 24% of Naphthalene selectivity, 2% of ethane selectivity, 6% of coke selectivity, and 7.0 μmol/g$_{catalyst}$/s of hydrogen generation rate.

Example 33

The 0.75 g 0.8 wt. % Ca-1.1 wt. % Fe@SiOC$_{0.5}$ catalyst prepared by Example 9 of the catalyst preparation method was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. And then the weight hourly space velocity (WHSV) of feed gas (5.0 vol. % H$_2$O, 85.5 vol. % CH$_4$ and 9.5 vol. % N$_2$) was adjusted to 10000 ml/g/h. After the WHSV being kept 20 mins, the reaction results were analyzed by the online chromatography. The results were as follows: 12.1% of methane conversion, 34.7% and 1.2 μmol/g$_{catalyst}$/s of ethylene selectivity and ethylene generation rate, 25.6% and 0.3 μmol/g$_{catalyst}$/s of benzene selectivity and benzene generation rate, 25.1% and 0.2 μmol/g$_{catalyst}$/s of Naphthalene selectivity and Naphthalene generation rate, 2.4% and 0.08 μmol/g$_{catalyst}$/s of ethane selectivity, 5.3% of CO selectivity, and 12 μmol/g$_{catalyst}$/s of hydrogen generation rate.

Example 34

The 0.75 g 0.5 wt. % Ca-0.5 wt. % Co@Si$_3$N$_4$ catalyst prepared by Example 11 of the catalyst preparation method was loaded in the fix-bed reactor, and then purged by Ar gas (25 ml/min) for 20 mins. Maintaining a constant flow rate of Ar, the reactor is programmed from room temperature up to 950° C. at a heating rate of 10° C./min. Then the weight hourly space velocity (WHSV) of feed gas (90 vol. % CH$_4$ and 10 vol. % N$_2$) was adjusted to 5000 ml/g/h. After the WHSV being kept 20 mins, the reaction results were analyzed by the online chromatography. The results were as follows: 14% of methane conversion, 40.1% and 1.3 μmol/g$_{catalyst}$/s of ethylene selectivity and ethylene generation rate, 22.3% and 0.3 μmol/g$_{catalyst}$/s of benzene selectivity and benzene generation rate, 26.2% and 0.2 μmol/g$_{catalyst}$/s of Naphthalene selectivity and Naphthalene generation rate, 11.4% of coke selectivity, and 8 μmol/g$_{catalyst}$/s of hydrogen generation rate.

Example 35

The 0.75 g 0.5 wt. % Co@SiOC$_{0.35}$N$_{0.2}$ catalyst prepared by Example 12 of the catalyst preparation method was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. And then the weight hourly space velocity (WHSV) of feed gas (90 vol. % $CH_4$ and 10 vol. % $N_2$) was adjusted to 4840 ml/g/h. After the WHSV being kept for 20 mins, the reaction results were analyzed by the online chromatography. The results were as follows: 16.2% of methane conversion, 46% and 1.4 µmol/$g_{catalyst}$/s of ethylene selectivity and ethylene generation rate, 27.5% and 0.35 µmol/$g_{catalyst}$/s of benzene selectivity and benzene generation rate, 26.5% and 0.3 µmol/$g_{catalyst}$/s of Naphthalene selectivity and Naphthalene generation rate, and 8 µmol/$g_{catalyst}$/s of hydrogen generation rate.

Example 36

The 0.75 g 0.5 wt. % $Co/SiO_2$ catalyst prepared by Example 13 of the catalyst preparation method was loaded in the fix-bed reactor, and then purged by Ar gas (25 ml/min) for 20 mins. Maintaining a constant flow rate of Ar, the reactor was programmed from room temperature up to 950° C. at a heating rate of 10° C./min. And then the weight hourly space velocity (WHSV) of the feed gas (90 vol. % $CH_4$ and 10 vol. % $N_2$) was adjusted to 4840 ml/g/h. After the WHSV being kept for 20 mins, the reaction results were analyzed by the online chromatography. The results were as follows: 18.5% of methane conversion, <3% of ethylene selectivity, <1% of benzene selectivity and Naphthalene selectivity, and >96% of coke selectivity.

In summary, under the conditions encountered in a fixed bed reactor (i.e. reaction temperature: 750~1200° C.; reaction pressure: atmospheric pressure; the weight hourly space velocity of feed gas: 1000~30000 ml/g/h; and fixed bed), conversion of methane is 8-50%. The selectivity of olefins is 30~90%. And selectivity of aromatics is 10~70%. There is no coking. The reaction process has many advantages, including a long catalyst life (>100 hrs), high stability of redox and hydrothermal properties under high temperature, high selectivity towards target products, zero coke deposition, easy separation of products, good reproducibility, safe and reliable operation, etc., all of which are very desirable for industrial application.

We claim:

1. A catalyst, comprising:
   a matrix of $Si_3N_4$, SiC, $SiC_xO_y$ (in which 4x+2y=4), $SiO_yN_z$ (in which 2y+3z=4), $SiC_xN_z$ (in which 4x+3z=4), or $SiC_xO_yN_z$ (in which 4x+2y+3z=4), with the proviso that the matrix is not $SiO_2$,
   one or more metal dopant(s) residing in the matrix,
   a plurality of active species, each of the plurality of active species is formed by replacing a Si, C, O, or N atom in the matrix with an individual atom metal dopant(s) atom so that the metal dopant(s) element is confined in a lattice of the doped matrix,
   wherein an amount of the metal dopant(s) ranges from 0.4 wt % to 1.9 wt % to of a total weight of the catalyst, wherein x ranges from 0 to 1, y ranges from 0 to 2, and z ranges from 0 to 4/3,
   wherein the catalyst is in an amorphous state,
   wherein the metal dopant(s) is selected from a group consisting of Li, Na, K, Mg, Al, Ca, Sr, Ba, Y, La, Ti, Zr, Ce, Cr, Mo, W, Re, Fe, Co, Ni, Cu, Zn, Ge, In, Sn, Pb, Bi, and Mn,
   and wherein the catalyst is active in converting methane to olefins.

2. The catalyst according to claim 1, wherein the catalyst further comprises one or more metals or metal compounds supported on a surface of the matrix, wherein the supported metal compound is selected from the group consisting of metal oxides, metal carbides, metal nitrides, metal silicides, and metal silicates.

3. The catalyst according to claim 2, wherein the supported metal or the metal in the supported metal compound is selected from the group consisting of Li, Na, K, Mg, Al, Ca, Sr, Ba, Y, La, Ti, Zr, Ce, Cr, Mo, W, Re, Fe, Co, Ni, Cu, Zn, Ge, In, Sn, Pb, Bi, and Mn.

4. The catalyst according to claim 1, wherein the catalyst is prepared by a chemical vapor deposition method comprising mixing silicon vapor or $SiCl_4$ with a vapor of the metal dopant(s) or a vapor of a volatile salt of the metal dopant(s); and reacting the mixture with a water vapor to obtain a solid.

5. The catalyst according to claim 1, wherein the catalyst is prepared by a vapor phase axial deposition method comprising mixing silicon vapor or $SiCl_4$ with a vapor of the metal dopant(s) or a vapor of a volatile salt of the metal dopant(s); exposing a substrate of corundum, silicon carbide, or silicon nitride to the mixture; and reacting the mixture with a water vapor to form a solid deposited on the substrate.

6. The catalyst according to claim 4, wherein the volatile metal salt is selected from the group consisting of metal carbonyls, metal alkoxides of carbon atom number from 1 to 5, and metal organic acid salts of C atom number from 1 to 5.

7. The catalyst according to claim 1, wherein the catalyst is in a form of particles of size in the range of 10 nm-10 cm.

8. The catalyst according to claim 1, wherein the amount of the metal dopant(s) ranges from 0.5 wt % to 1.6 wt % of a total weight of the catalyst.

9. The catalyst according to claim 1, wherein the individual metal dopant(s) atom in each of the plurality of active species bonds with atoms adjacent to the replaced Si, C, O, or N atom.

10. The catalyst according to claim 1, wherein the metal dopant(s) is a transition metal.

11. The catalyst according to claim 1, wherein the metal dopant(s) is Fe or Co.

12. A method of conversion of methane to olefins, comprising:
   reacting a methane feedstock comprising methane in presence of a catalyst of claim 1; and
   obtaining a product stream comprising olefins, aromatics, and hydrogen.

13. The method according to claim 12, wherein a reaction temperature ranges from 750° C. and 1200° C.

14. The method according to claim 12, further comprising a step of pretreating the catalyst in a feed gas comprising hydrocarbons selected from the group consisting of alkanes with 2 to 10 carbon atoms, alkenes with 2 to 10 carbon atoms, alkyne with 2 to 10 carbon atoms, monohydric alcohol with 1 to 10 carbon atoms, dihydric alcohol with 2 to 10 carbon atoms, aldehyde with 1 to 10 carbon atoms, carboxylic acid with 1 to 10 carbon atoms, and aromatics with 6 to 10 carbon atoms, at a temperature ranging from 800° C. to 1000° C. under a pressure ranging from 0.1 MPa to 1 MPa in a weight hourly space velocity of feed gas ranging from 500 ml/g/h to 3000 ml/g/h.

15. The method according to claim 12, wherein the methane feedstock comprises methane, optionally an inert gas, optionally a non-inert gas, and is substantially oxygen free, wherein the inert gases is selected from a group consisting of nitrogen (N$_2$), helium (He), neon (Ne), argon (Ar), krypton (Ke), and a mixture thereof, wherein the non-inert gases is selected from a group consisting carbon monoxide (CO), hydrogen (H$_2$), carbon dioxide (CO$_2$), water vapor (H$_2$O), monohydric alcohol with 1 to 5 carbon atoms, dihydric alcohol with 2 to 5 carbon atoms, alkanes with 2 to 8 carbon atoms, and a mixture thereof.

16. The method according to claim 12, wherein the conversion of methane is carried out in a fluidized bed, a moving bed, or a fixed bed, at a pressure ranging from 0.05 MPa to 1 MPa, and a weight hourly space velocity of the methane feedstock ranging from 1000 ml/g/h to 30000 ml/g/h.

17. The method according to claim 12, wherein the metal dopant is selected from the group consisting of alkali metals, alkaline earth metals, and transition metals.

18. The method according to claim 15, wherein the methane feedstock comprises 5-100% of methane by volume, 0 to 95% of inert gas by volume, and 0-15% of the non-inert gas by volume.

19. A method of preparing a catalyst of claim 1, comprising the steps of:

dissolving a liquid silicon source and a metal salt selected from the group consisting of metal nitrates, metal halides, metal sulfates, metal carbonates, metal hydroxides, metal organic acid salts having 1 to 10 carbon atoms, and metal alkoxides having 1 to 10 carbon atoms in a mixture of water and ethanol wherein a weight content of water in the mixture is 10-100%;

obtaining a sol gel from the mixture after hydrolysis and condensation;

drying the slurry to obtain a powder;

melting the powder at a temperature ranging from 1300° C. to 2000° C. to a molten mixture;

cooling the molten mixture to a solid; and grinding the solid to particles.

20. A method for preparing a catalyst according to claim 1, comprising the steps of:

providing a porous silicon-based material selected from the group consisting of silica, silicon carbide, silicon nitride, and a mixture thereof;

impregnating the porous silicon-based material in a solution comprising a salt of the metal dopant to obtain a slurry;

drying the slurry to obtain a powder;

melting the powder at a temperature ranging from 1300° C. to 2000° C. to a molten mixture; and cooling the molten mixture to a solid.

* * * * *